United States Patent [19]

Hiratani et al.

[11] Patent Number: 4,946,785

[45] Date of Patent: Aug. 7, 1990

[54] METHOD OF SUPPRESSING THE THERMAL DEGRADATION OF UROKINASE

[75] Inventors: Hajime Hiratani, Sennan, Japan; Satoshi Nishimuro, Birmingham, Ala.; Koichiro Nakanishi, Kobe; Masaichi Ota, Nishinomiya; Hiroshi Matsumoto, Ashiya, all of Japan

[73] Assignee: Japan Chemical Research Co., Ltd., Hyogo, Japan

[21] Appl. No.: 208,156

[22] Filed: Jun. 17, 1988

[30] Foreign Application Priority Data

Jun. 18, 1987 [JP] Japan .................................. 62-153043

[51] Int. Cl.$^5$ ........................... C12N 9/96; C12N 9/72
[52] U.S. Cl. .................................... 435/188; 435/215; 435/236

[58] Field of Search ............... 435/188, 215, 236, 238; 424/101, 94.64, 94.63

[56] References Cited

U.S. PATENT DOCUMENTS 4,361,652 11/1982 Uemura et al. ...................... 435/188
4,404,187 9/1983 Schwinn et al. ..................... 424/101

FOREIGN PATENT DOCUMENTS 200966 11/1986 European Pat. Off. .

Primary Examiner—Richard A. Schwartz
Assistant Examiner—Mary E. Mosher
Attorney, Agent, or Firm—Burgess, Ryan & Wayne

[57] ABSTRACT

The thermal degradation of urokinase in an aqueous solution is suppressed by heating an aqueous solution containing urokinase in the presence of citric acid or a water-soluble salt thereof such as sodium, potassium or lithium citrate at about 60° C. for about 10 hours.

5 Claims, No Drawings

METHOD OF SUPPRESSING THE THERMAL DEGRADATION OF UROKINASE

BACKGROUND OF THE INVENTION

1. Field of the Invention

The present invention relates to a method of producing urokinase preparations. In more particular, the invention is concerned with a method of preventing the degradation of urokinase to be caused when an aqueous solution of urokinase is for example heated at 60° C. for 10 hours to inactivate pathogenic viruses.

2. Description of the Related Art

Urokinase is a plasminogen activating factor which exists in small quantities in urine and, with its fibrinolytic activity, has nowadays been put in wide use for the therapy of thrombosis. Urokinase dates as far back as 1800's when the existence in urine of a substance having fibrinolytic activity was already recognized by Stahli, Gehrig, et al. As recently as 1952, the plasminogen activator was designated "urokinase" (hereinafter referred to briefly as "UK") by Sobel. In 1957, Ploug nearly completed the method of determining activity of this substance as well as the procedure of separating and purifying the same from urine, thereby laying down the foundation for its clinical application to the therapy of thrombosis [Ploug, J.: Biochim. Biophys. Acta, 24, 278 (1957)]. Thereafter, White clarified that UK is a substance consisting of two components but not a single component substance: namely, there exist high-molecular type urokinase (hereinafter referred to as "H-UK") having a molecular weight of 54,000 and low-molecular type urokinase (hereinafter referred to as "L-UK") having a molecular weight of 32,000, and it was found that the only the former is contained in urine immediately discharged from human body, whereas the latter is produced from the former through decomposition and cleavage by proteolytic enzymes such as uropepsin taking place during storage, extraction or purification of urine [White, W. F. et al: Biochemistry,, 5, 2160 (1966)]. Consequently, it can be said that the currently available urokinase preparations contain the mixtures of H-UK and L-UK, though their ratio varies widely.

Now referring to the above-described two kinds of urokinase, H-UK and L-UK, in terms of comparison of their performances, determination by way of the ordinary determination methods, such as the fibrin plate method, fibrin tube method [Ploug, J., et al.: Biochim. Biophys. Acta, 24, 278 (1957)] or AGLME synthetic substrate method [Johnson, A. J. et al.: Thromb. Diath. Haemorrh., 21, 259 (1969)], indicates that the pure compounds of H-UK and L-HK show approximately the same level of activity per mmole, but on the other hand, Chandler-Poole method [Chandler, A. B.: Lab. Invest., 7, 110 (1957). Poole, J. C. F.: Q. J. Exp. Physiol., 44, 372 (1959)] which is the nearest to the thrombolytic action in vivo and the method using the naturally occurring compound of glutamylplasminogen (Japanese Patent Application Laid-open No. 130485/1978) demonstrate that H-UK exhibits a level of activity nearly double that of L-UK. This means that H-UK, when put into clinical application in almost half an amount can produce the effects equal to L-UK, and can prevent unexpected side-effects such as bleeding (Japanese Patent Application Laid-open No. 130485/1978). H-UK is known to provide a variety of additional advantages, and currently, in Europe and America as well as in Japan, the standards covering the urokinase preparations specify that the content of H-UK is not to be less than 75%.

On the other hand, it is a matter of common knowledge that hepatitis virus and other pathogenic viruses are present in human blood, organs and urine. Therefore, the UK preparations produced from human urine, when administered to human being as such, provides the possibility of being affected with viral infections. Both in U.S.A. and Japan at present, the obligation has been placed to perform heat treatment at 60° C. for 10 hours of the UK preparations for the purpose of inactivation of pathogenic viruses.

Since such heat treatment at 60° C. for 10 hours of UK solutions results in reduction of activity of UK, however, various means have been conducted into practice for the prevention of reduction of activity. Actually adopted are the methods of adding on the occasion of heat treatment amino acids, saccharides, salts, gelatin, human serum albumin, hydroxypropylcellulose, etc. The Japanese Patent Application Laid-Open Nos. 43233/1981, 142592/1978 and 2391/1981). The above-described methods can prevent reduction of the UK activity to be caused by heat treatment at 60° C. for 10 hours but only to a limited degree.

SUMMARY OF THE INVENTION

The present inventors, after repeated intensive experiments on the above-described heat treatment, unexpectedly found that the degradation of UK takes place during such heat treatment and that this phenomenon cannot be prevented with any of the above-mentioned heat stabilizers as described below. During heat treatment, the degradation of UK proceeds, even though the reduction of the UK activity can be prevented with heat stabilizers, and when the content of H-UK decreases below 75%, the resulting preparation falls out of the specifications and cannot help being discarded. In consequence, the degradation presents the problem of greater importance than reduction of the UK activity.

In view of the above, the present inventors conducted laborious research over and over again, and as a result reached the solution for this problem, leading to the completion of this invention.

Thus, UK solutions of different pH values ranging from pH 2 to pH 10 were prepared and subjected to heat treatment at 60° C. for 10 hours, whereupon retention rates of UK activity and H-UK content were measured in parallel (refer to Experiment Example 1, Table 1, Experiment Example 2 and Table 2). As a result, it was found that the relatively higher pH range of pH 6.5 to 7.0 is desirable for securing the retention rate of UK activity, whereas the comparatively lower pH range of pH 3.0 to 4.0 is optimal for preventing the reduction of H-UK content. That is to say, our research led us to the finding that the optimal conditions each for securing the activity retention rate and for maintaining the H-UK content retention rate are completely contradictory.

Such being the case, it was tried to carry out heat treatment in the low pH range with the addition of human serum albumin, gelatin, amino acids, etc., with the result that the slight lowering of pH brings about the remarkable reduction of the activity retention ratio, and the attempt turned out to be unsuccessful (refer to Experiment Example 8 and Table 3). Then, various attempts were made to search for a method capable of maintaining the H-UK content even when heat treatment is carried out at 60° C. for 10 hours under the optimal conditions of pH 6 to 7 for the activity retention rate, and as a result, it turned out that addition in small amounts of aqueous citric acid salt or citric acid can prevent the degradation of H-UK even under the optimal conditions for the activity retention rate (refer to Experiment Example 4 and Table 4).

The present invention has been completed on the basis of the above-described novel finding and is concerned with a method of suppressing the degradation of urokinase to be brought about by heating, characterized in that the said method comprises conducting heat treatment of an aqueous solution containing urokinase in the presence of citric acid or its aqueous salt.

DETAILED DESCRIPTION OF THE INVENTION

As the aqueous citric acid salt, there may be mentioned, for example, sodium citrate ($Na_3C_6H_5O_7.2H_2O$) and its acid salt ($Na_2HC_6H_5O_7$), potassium citrate ($K_3C_6H_7O_7.H_2O$) and its acid salt ($KH_2C_6H_5O_7$), ammonium citrate (($NH_4)_3C_6H_5O_7$) and its acid salt (($NH_4)_2HC_6H_5O_7$), and lithium citrate ($Li_3C_6H_5O_7.4H_2O$). These may be used as a mixture of not less than two kinds. The addition level of citrate or citric acid is preferably 0.1 to 0.5% (as sodium citrate) of the UK solution. In other words, other salts or citric acid is desirably used in quantities corresponding to the above amount of sodium citrate as converted on the molecular weight ratio. The degree of purification for UK to be employed is not specifically limited but may be preferably not less than 1,000 IU (international unit)/mg protein of specific activity, more preferably not less than 10,000 IU/mg protein, while the pH of the UK solution is desirably maintained at 6.0 to 7.0 in order to raise the activity retention ratio as far as possible. Suitable pH would be 6.0 to 7.5.

The conditions of heat treatment is preferably about 60° C. and about 10 hours in conformity with 60° C. and 10 hours specified in the standards for UK preparations. Nevertheless, other conditions falling out of the above described ranges may be applied to the heat treatment, depending upon the intended purpose and only if variations in UK activity and H-UK content caused by such conditions are acceptable.

Heat treatment under simultaneous addition of a citric acid salt and human serum albumin, followed by sterile filtration through a membrane filter, served to prevent UK from being adsorbed onto the filter, and produced excellent results (Example 4).

EXPERIMENT EXAMPLE 1

High-purity urokinase (hereinafter referred to briefly as "UK") with specific activity of 129,400 IU/mg protein (hereinafter referred to briefly as "IU/mg-pro.") and a high-molecular urokinase content of 94.4% was dissolved in 0.2 M phosphate buffer containing 0.15M sodium chloride to a concentration of 0.7 mg/ml. Prepared from the solution were nine kinds of UK solutions having a pH value adjusted to 2, 3, 4, 5, 6, 7, 8, 9 and 10, respectively, which were then subjected to heat treatment at 60° C. for 10 hours, followed by measurement of the retained UK activities (Note 1) and H-UK contents (Note 2).

Note 1:
Measurement of the retained UK activity; Measurement was performed with the fibrin test tube method of J. Ploug [Biochim. Biophys. Acta; 24, 278 (1957)]

Note 2:
Measurement of the H-UK content;

Measurement was carried out by means of gel permeation method using a high performance liquid chromatograph which consisted of a liquid feeding unit LC-6A and Chromato-Pack CR-3A for high performance liquid chromatography (manufactured by Shimadzu Seisakusho Co. of Japan, Kyoto) as well as column for gel chromatography SW-3000 (manufactured by Toyo Soda Ind. of Japan, Tokyo) in combination.

The above-described two measurement methods were adopted in the Experiment Examples and Examples to be stated in the following.

TABLE 1

| pH | Activity retention rate* % | H-UK content retention rate**, % |
|---|---|---|
| 2 | 35 | 94.5 |
| 3 | 48 | 101.5 |
| 4 | 62 | 101.5 |
| 5 | 40 | 89.7 |
| 6 | 79 | 88.8 |
| 7 | 83 | 83.9 |
| 8 | 30 | 9.2*** |
| 9 | 0 | 0 |
| 10 | 0 | 0 |

Note
*The UK activity prior to heat treatment of the test solution was taken as 100.
**The H-UK content prior to heat treatment of the test solution was taken as 100.
***Supposedly because UK underwent a polymerization reaction during heating, the eluate was less in volume at the RT position of H-UK.

EXPERIMENT EXAMPLE 2

Using high-purity UK with specific activity of 148,00 IU/mg-pro. and H-UK content of 97.2%, the same experiment as described in Experiment Example 1 was carried out at pH·values of 6.0, 6.5 and 7.0, respectively, with the results being shown in Table 2.

TABLE 2

| pH | Activity retention rate*, % | H-UK content retention rate**, % |
|---|---|---|
| 6.0 | 72 | 92.0 |
| 6.5 | 84 | 85.2 |
| 7.0 | 88 | 80.4 |

Note
*The UK activity prior to heat treatment of the test solution was taken as 100.
**The H-UK content prior to heat treatment of the test solution was taken as 100.

EXPERIMENT EXAMPLE 3

High-purity UK with specific activity of 145,300 IU/mg-pro. and H-UK content of 97.2% was dissolved in 0.2M phosphate buffer containing 0.15M sodium chloride to a concentration of 0.7 mg/ml. After adding separately to the solution 0.3% of human serum albumin, 0.3% of gelatin, 1.5% of lysine and 2% of hydroxypropylcellulose 50000, heat treatment (60° C. for 10 hours) was carried out with each of different solutions at a pH value adjusted to 6.0 and 7.0, respectively, to measure the UK activities and H-UK contents. The results are shown in Table 3.

TABLE 3

| Additive | pH | Activity retention rate*, % | H-UK content retention rate**, % |
|---|---|---|---|
| None | 6.0 | 69 | 90.2 |
|  | 7.0 | 86 | 79.6 |
| 0.3% of human serum albumin | 6.0 | 87 | 89.6 |
|  | 7.0 | 93 | 79.4 |
| 0.3% of gelatin | 6.0 | 70 | 90.7 |
|  | 7.0 | 84 | 78.7 |
| 1.5% of lysine | 6.0 | 67 | 87.0 |
|  | 7.0 | 84 | 80.0 |
| 2% of hydroxy- | 6.0 | 65 | 85.0 |

TABLE 3-continued

| Additive | pH | Activity retention rate*, % | H-UK content retention rate**, % |
|---|---|---|---|
| propylcellulose 50000 | 7.0 | 85 | 79.2 |

Note
*The UK activity prior to heat treatment of the test solution was taken as 100.
**The H-UK content prior to heat treatment of the test solution was taken as 100.

EXPERIMENT EXAMPLE 4

High-purity UK with specific activity of 145,300 IU/mg-pro. and H-UK content of 97.2% was brought into a solution having a concentration of 0.7 mg/ml, and sodium citrate was added to the solution to different concentrations of 0.1, 0.25 and 0.5%, respectively. Each of the resulting test solutions was adjusted to pH values of 6.0, 6.5 and 7.0, individually, followed by heat treatment (at 60° C. for 10 hours) to measure the UK activities and H-UK The results are shown in Table 4.

TABLE 4

| pH | Added sodium citrate, % | Activity retention rate*, % | H-UK content retention rate**, % |
|---|---|---|---|
| 6.0 | 0 | 68 | 88.9 |
|  | 0.1 | 70 | 94.3 |
|  | 0.25 | 68 | 94.7 |
|  | 0.5 | 71 | 94.7 |
| 6.5 | 0 | 81 | 81.2 |
|  | 0.1 | 80 | 89.8 |
|  | 0.25 | 82 | 90.7 |
|  | 0.5 | 81 | 90.2 |
| 7.0 | 0 | 84 | 79.0 |
|  | 0.1 | 82 | 85.0 |
|  | 0.25 | 84 | 86.0 |
|  | 0.5 | 85 | 86.5 |

Note
*The UK activity prior to heat treatment of the test solution was taken as 100.
**The H-Uk content prior to heat treatment of the test solution was taken as 100.

EXAMPLE 1

A 150 mg portion of high-purity UK with specific activity of 121,600 IU/mg-pro. and H-UK content of 95.2% was dissolved in 100 ml of 0.2M sodium phosphate solution containing 0.1 M sodium chloride, and citric acid was added to the solution to a concentration of 0.1%. The test solution was adjusted to a pH value of 6.0, followed by heat treatment at 60° C. for 10 hours and cooling to measure the UK activity and H-UK content. As a result, it was found out that the UK activity and H-UK content retention rates were 69% and 91%, respectively.

EXAMPLE 2

UK with specific activity of 121,600 IU/mg-pro. and H-UK content of 95.2% was dissolved in 0.2M phosphate buffer containing 0.15 M sodium chloride to prepare 1,000 ml of a 1,800,000 IU/ml concentrated UK solution. The solution was admixed with sodium citrate to a concentration of 0.1%, then adjusted to pH 6.0, subjected to heat treatment at 60° C. for 10 hours and immediately cooled with ice. The treated solution was subjected to gel-column chromatography with the use of Sephadex G-100 to remove the sodium citrate, subsequently filtered for microbe removal through a membrane filter with a pore size of 0.22 micrometer and filled in 2 ml portions into vials, followed by lyophilization. As compared to the original UK solution prior to heat treatment, the final UK preparation was found to show a UK activity retention rate of 73% and an H-UK content retention rate (with the H-UK content prior to heat treatment being taken as 100%) of 90.0%.

EXAMPLE 3

UK with specific activity of 166,400 IU/mg-pro. and H-UK content of 82% was dissolved in 0.2 M phosphate buffer containing 0.15 M sodium chloride to a concentration of 0.7 mg/ml to prepare 50 ml of a UK solution, to which potassium citrate was added to a concentration of 0.3%. The test solution was divided into two portions being called "Solution A" and "Solution B".

Solution A was adjusted to pH 6.0, while Solution B to pH 7.0, and both of them were subjected to heat treatment at 60° C. for 10 hours and then cooled to measure the UK activities and H-UK contents, with the results being shown in Table 5.

TABLE 5

|  | Activity retention rate*, % | H-UK content retention ratio***, % | H-UK content retention rate**, % |
|---|---|---|---|
| Solution A (pH 6.0) | 67 | 76 | 92.6 |
| Solution B (pH 7.0) | 84 | 68 | 83.0 |

Note
*The UK activity prior to heat treatment of the test solution was taken as 100.
**The H-UK content prior to heat treatment of the test solution was taken as 100.
***The sum of the L-UK and H-UK contents in the test solution after heat treatment was taken as 100.

EXAMPLE 4

An aqueous solution of UK with specific activity of 153,000 IU/mg and H-UK content of 93.6% (500,000 IU/ml=3.27 mg/ml) was admixed with sodium citrate, human serum albumin and sodium phosphate to respective concentrations of 0.1%, 0.3% and 0.2M, and the solution was adjusted to pH 6.0 and subjected to heat treatment at 60° C. for 10 hours, followed by immediate ice-cooling. The UK solution was allowed to to undergo a microbe-removal filtration procedure with use of a membrane filter with a pore size of 0.22 micrometer and the filtrate was diluted with sterile physiological saline to prepare urokinase solutions of 60,000 IU/ml concentration, followed by lyophilization. As compared to the original UK solution prior to heat treatment, the final UK preparation was found to provide a recovery rate of 92% and H-UK content retention rate of 90.6% (with the H-UK content prior to heat treatment being taken as 100%).

We claim:
1. A method for suppressing the thermal degradation of urokinase in an aqueous solution, which method consists essentially of heating a urokinase-containing aqueous solution at about 60° C. for at least 10 hours, while maintaining its pH at 6.0 to 7.5, in the presence of citric acid or a water-soluble salt thereof, in a concentration corresponding to 0.1 to 0.5% calculated as sodium citrate.
2. A method according to claim 1, wherein the water-soluble salt of citric acid is sodium, potassium or lithium citrate.
3. The method of claim 1 wherein said water-soluble salt is sodium citrate.
4. The method of claim 1 wherein said water-soluble salt is potassium citrate.
5. The method of claim 1 wherein said aqueous solution contains citric acid.

* * * * *